(12) United States Patent
De Souza Russo et al.

(10) Patent No.: US 7,148,350 B2
(45) Date of Patent: Dec. 12, 2006

(54) COMPOUNDS IN THE FORM OF HOMODIMERIC OR HETERODIMERIC PRO-DRUGS; PROCESS FOR OBTAINING THESE PRO-DRUGS AND THEIR ACCEPTABLE PHARMACEUTICAL SALTS AND USE OF COMPOUNDS IN THE TREATMENT OF PHOSPHODIESTERASES-MEDIATED DISEASES OR DYSFUNCTION

(75) Inventors: Elisa Mannochio De Souza Russo, Itapira (BR); Valter Freire Torres Russo, Itapira (BR)

(73) Assignees: Cristalia Prod.Qui.Farm. LTDA, Itapira (BR); Ogari Pacheco, Itapira (BR)

( * ) Notice: Subject to any disclaimer, the term of this patent is extended or adjusted under 35 U.S.C. 154(b) by 23 days.

(21) Appl. No.: 10/362,602

(22) PCT Filed: Aug. 7, 2001

(86) PCT No.: PCT/BR01/00096

§ 371 (c)(1),
(2), (4) Date: Mar. 21, 2003

(87) PCT Pub. No.: WO02/12241

PCT Pub. Date: Feb. 14, 2002

(65) Prior Publication Data

US 2004/0106629 A1 Jun. 3, 2004

(30) Foreign Application Priority Data

Aug. 8, 2000 (BR) .................................... 0003386

(51) Int. Cl.
*C07D 487/04* (2006.01)
*A61K 31/519* (2006.01)
*A61P 15/10* (2006.01)

(52) U.S. Cl. ............... 544/262; 514/252.16; 514/262.1
(58) Field of Classification Search ........... 514/252.16, 514/262.1; 544/262
See application file for complete search history.

(56) References Cited

U.S. PATENT DOCUMENTS

| | | |
|---|---|---|
| 4,127,118 A | 11/1978 | Latorre |
| 4,631,190 A | 12/1986 | Shen et al. |
| 4,801,587 A | 1/1989 | Voss et al. |
| 4,863,911 A | 9/1989 | Anderson, Jr. et al. |
| 4,997,913 A | 3/1991 | Hellstrom et al. |
| 5,059,603 A | 10/1991 | Rubin |
| 5,140,013 A | 8/1992 | Gaudreault et al. |
| 5,306,809 A | 4/1994 | Boon et al. |
| 5,981,563 A | 11/1999 | Lowrey |
| 6,030,997 A | 2/2000 | Eilat et al. |
| 6,031,096 A | 2/2000 | Glazier et al. |
| 6,037,346 A | 3/2000 | Doherty, Jr. et al. |
| 6,040,297 A | 3/2000 | De Flora et al. |
| 6,051,576 A | 4/2000 | Ashton et al. |

FOREIGN PATENT DOCUMENTS

| | | |
|---|---|---|
| DE | 198 34 505 A1 | 2/2000 |
| DE | 198 34 506 A1 | 2/2000 |
| DE | 198 34 507 A1 | 2/2000 |
| WO | WO 99/59584 A1 | 11/1999 |
| WO | WO 99/60985 A2 | 12/1999 |
| WO | WO 99/64033 A1 | 12/1999 |
| WO | WO 99/66924 A1 | 12/1999 |
| WO | WO 99/66933 A1 | 12/1999 |
| WO | WO 00/00199 A1 | 1/2000 |

OTHER PUBLICATIONS

Wolff, Manfred E. "Burger's Medicinal Chemistry, 5ed, Part I", John Wiley & Sons, 1995, pp. 975-977.*

(Continued)

*Primary Examiner*—Thomas C. McKenzie
(74) *Attorney, Agent, or Firm*—Birch, Stewart, Kolasch & Birch LLP (57) ABSTRACT

The present invention describes new homo or heterodimer prodrugs wherein both active monomeric units are compounds of the formula:

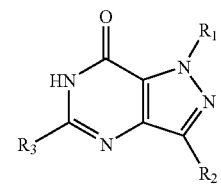

where $R_1$ and $R_2$ are each independently —H, —$C_1$–$C_6$ alkyl —$C_1$–$C_6$OH, or —$C_1$–$C_6$NHR', wherein R' is —H, or —$C_1$–$C_6$ alkyl, $R_3$ is:

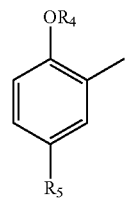

where $R_4$ and $R_5$ are defined in the description. The monomeric units are coupled to each other via a labile carbonate (—O—COO—), carbamate (—O—CO—N—), urea (—N—CO—N—) or phosphate (—O—POO—O—) moiety. Such homo or heterodimer prodrugs are useful in the treatment of erectile dysfunction.

35 Claims, 2 Drawing Sheets

OTHER PUBLICATIONS

Banker, G.S. et al, "Modern Pharmaceutics, 3ed.", Marcel Dekker, New York, 1996, pp. 451 and 596.*

Pan-Zhou et al., Antimicrobial Agents and Chemotherapy, vol. 41, No. 11, pp. 2502-2510 (Nov. 1997).

Zhou et al., J. Clin. Pharmacol., vol. 37, pp. 201-213 (1997).

Wright et al., Clinical Pharmacology & Therapeutics, p. 184 (Feb. 1996).

Lawless, J Am Board Fam Pract, vol. 11, No. 4, pp. 307-314 (1998).

Schinazi et al., Antimicrobial Agents and Chemotherapy, vol. 34, No. 6, pp. 1061-1067 (Jun. 1990).

* cited by examiner

COMPOUNDS IN THE FORM OF HOMODIMERIC OR HETERODIMERIC PRO-DRUGS; PROCESS FOR OBTAINING THESE PRO-DRUGS AND THEIR ACCEPTABLE PHARMACEUTICAL SALTS AND USE OF COMPOUNDS IN THE TREATMENT OF PHOSPHODIESTERASES-MEDIATED DISEASES OR DYSFUNCTION

This application is the national phase under 35 U.S.C. § 371 of PCT International Application No. PCT/BR01/00096 which has an International filing date of Aug. 7, 2001, which designated the United States of America.

The present invention describes the synthesis and pharmaceutical application of compounds in the form of homo or heterodimeric pro-drugs and their salts, effective in the treatment of phosphodiesterases-mediated diseases and dysfunction, or therapeutic studies induced by these enzymes' inhibition.

These compounds are particularly useful in the treatment of erectile dysfunction, disturbance that afflicts from five to ten percent of world population.

Erectile dysfunction is defined as the persistent disabling in achieving or maintaining the penis erection with sufficient tumescence to allow a satisfactory sexual intercourse.

Although it is not a fatal condition, the disability to keep satisfactory sexual relations deeply affects the life quality of the patients, as well as the life of their partner, causing considerable emotional and psychological morbidity to the concerned parties. (Lawless C; Cree J—J. Am. Board Fam. Pract., 11(4):307–314—Oral medications in the management of erectile dysfunction).

Several causes can lead to an erectile dysfunction. Different mechanisms are involved, comprehending organic and psychological conditions. Basically, they can be related to three main groups:

Group 1—Erectile Dysfunction Resulting from Organic Factors.

Resulting from an acute or chronic physiologic condition, including endocrinologic, neurologic or vascular ethiologies. About 80% of the cases are secondary to organic diseases, being 70% of those cases due to arterial or venous abnormalities.

Group 2—Erectile Dysfunction Arising from Psychogenic Factors:

The more common causes associated to erectile dysfunction of psychogenic cause are related to performance anxiety, relationship conflicts and sexual inhibitions, among others. Psychogenic factors often coexist with organic causes.

Group 3—Erectile Dysfunction Arising from Iatrogenic Factors:

Erectile dysfunction from iatrogenic cause results of medical or surgical therapy intended to heal other disorders. The most frequent surgical cause is the prostate removal in cases of cancer.

Possibilities for treatment of erectile dysfunction are inter-related with the mechanism involved in the process of penis erection.

The triggering process for erection is a neurogenic event. Pulses can originate from brain or can derive from sacral reflexes (as we can see in paraplegic patients). Under normal circumstances, the combination of both of them promotes the triggering effect.

Dilatations or cavernous arteries and of helicinal arteries are controlled by a very known neural regulation mechanism. However, they are not enough for the development of a rigid erection, due to the escapes for the venous stream and due to the fact that the resistance of lacunal spaces of cavernous bodies depends on the smooth musculature tonus. The relaxation of smooth muscles is necessary in order to allow the cavernous bodies expansion. Parasympathetic pulses start this relaxation. This way, sympathetic tonus, contracting the smooth musculature, must be reduced.

After the first pulses, the poorly innervated endothelial cells network and from smooth musculature, manage their own coordination, in order to relax all the cells at the same time. The nitric oxide is considered to have a crucial role for triggering these events. This relaxation allows a free blood flow to the inside of lacunas, finally resulting in such a tumescence that the outlet blood flow will be blocked by the compression of venous channels present between distended body tissue and the albuginea tunic. This leads to the penis rigidity that can also be implemented by the contraction of the pelvic floor muscles, compressing the crurals of cavernous bodies, reaching a pressure higher than the blood pressure. By this time, the blood escape from cavernous bodies is minimum.

The end of erection occurs by means of another contraction of the smooth musculature, started by sympathetic pulses and by the production of substances such as endotheline-1, the prostaglandine $F_{2\alpha}$ and tromboxan $A_2$ by endothelial cells. This allows the venous flow to outside the penis due to the decompression of subtunical venous plexus.

Endothelial cells produce both vasodilative substance, among them the prostacyline and the nitric oxide, and vasoconstrictor substances. The nitric acid has been described as propagator of a series of events resulting in the relaxation of all cells of smooth musculature of cavernous bodies. It is synthesized from arginine by a varied number of nitric oxide synthases. An isoform normally expressed in the endothelial cells is the calcium-dependent, and can be activated by several stimulus, hormones and by agonists receptor-mediated, such as acetylcholine and bradicinine. The nitric oxide exerts its effect on smooth vascular cells, onto which it diffuses, linking with guanylate cyclase enzyme, residing in this cells cytoplasm. This enzyme, upon activation, converts the nucleotide guanosine trifophosphate into cyclic guanosine monophosphate (cGMP). With the increase of the intracellular levels of GMP, the intracellular calcium levels decrease, leading to cell relaxation, which causes dilatation of musculature. The termination of the cGMP action occurs by means of the actuation of the enzyme named phosphodiesterase V-type. (PDE-V) present in cavernous bodies, which converts cGMP into GMP (guanosine monophosphate).

Prostacycline is another endothelium-dependent vasodilator substance, acting with the purpose of increasing the concentration of cyclical adenosine monophosphate (cAMP) from Adenosine Triphosphate. A cAMP can also lead to relaxation of the smooth musculature the same way cGMP does.

Presently, the patients with erectile dysfunction count on several options for their treatment. They comprehend psychological advice therapies for emotional causes, the use of mechanical vacuum devices, surgical implant, therapies by injectable drugs administration in penis cavernous bodies, intra-urethral, topic and also oral therapy for organic, emotional and associated causes.

Mechanical vacuum devices consist of a plastic cylinder placed in the penis, which causes erection when the air is removed from inside it by means of a vacuum pump. These machines are reliable and safe. However, patients present restriction to the use of these devices, due to the need of interruption of sexual act, in addition to the non-spontaneity of erection.

Drugs applied directly in the cavernous bodies consist of injectable vasoactive substances, which act to expand the arteries and to relax the cavernous body tissues. These drugs produce a firm erection between 5 to 15 minutes after injection. Since the patient has learnt correctly the technique, the injection of these substances is simple and generally causes no pain. However, frequently we see cases of long and painful erections, and the patient has to search for medical help in order to revert them. Among other problems associated to injectable therapies are fear, pain and the occurrence of fibrosis of the penis tissues, factors that lead to the necessity of treatment interruption.

Another option for the treatment of erectile dysfunction consists of the implantation of a surgically implanted prosthesis. The implantation of these prostheses does not interfere with normal organic functions, and they present the advantage of patient being able to get immediate erections, when necessary. However, there is always the risk associated with complications that can result in the need of implant removal. There is also a negative psychological factor associated with implants, which refer, again, to the fact that the erection phenomenon is not natural or spontaneous. Due to the character highly invasive and irreversible of these implants, they are recommended as final option for the treatment of erectile dysfunction.

Therapy with administration of drugs orally is a treatment means that is not much invasive and very well tolerated by patients. In addition, most of times, it shows to present transient side effects when medications are correctly used. Due to the wide acceptance of patients related to this kind of therapy, researchers have tried to develop drugs more and more efficient for the treatment of erectile dysfunction that use this path of administration.

Yohimbine is the oldest medication used for treating the erectile dysfunction, by oral administration. From the beginning of its use, it has shown conflicting results related to its effectiveness. More recent research shows that its effectiveness is low in the treatment of patients with organic erectile dysfunction.

Recently, other medications were launched for the treatment of erectile dysfunction by oral path. Among them, there are specific phosphodiesterases-inhibitors type V, which is the isoform of the enzyme class, called phosphodiesterases, mainly in the penis. The most known example among the drugs acting this way is the sildenafil.

DETAILED DESCRIPTION OF THE INVENTION

Figure 1:
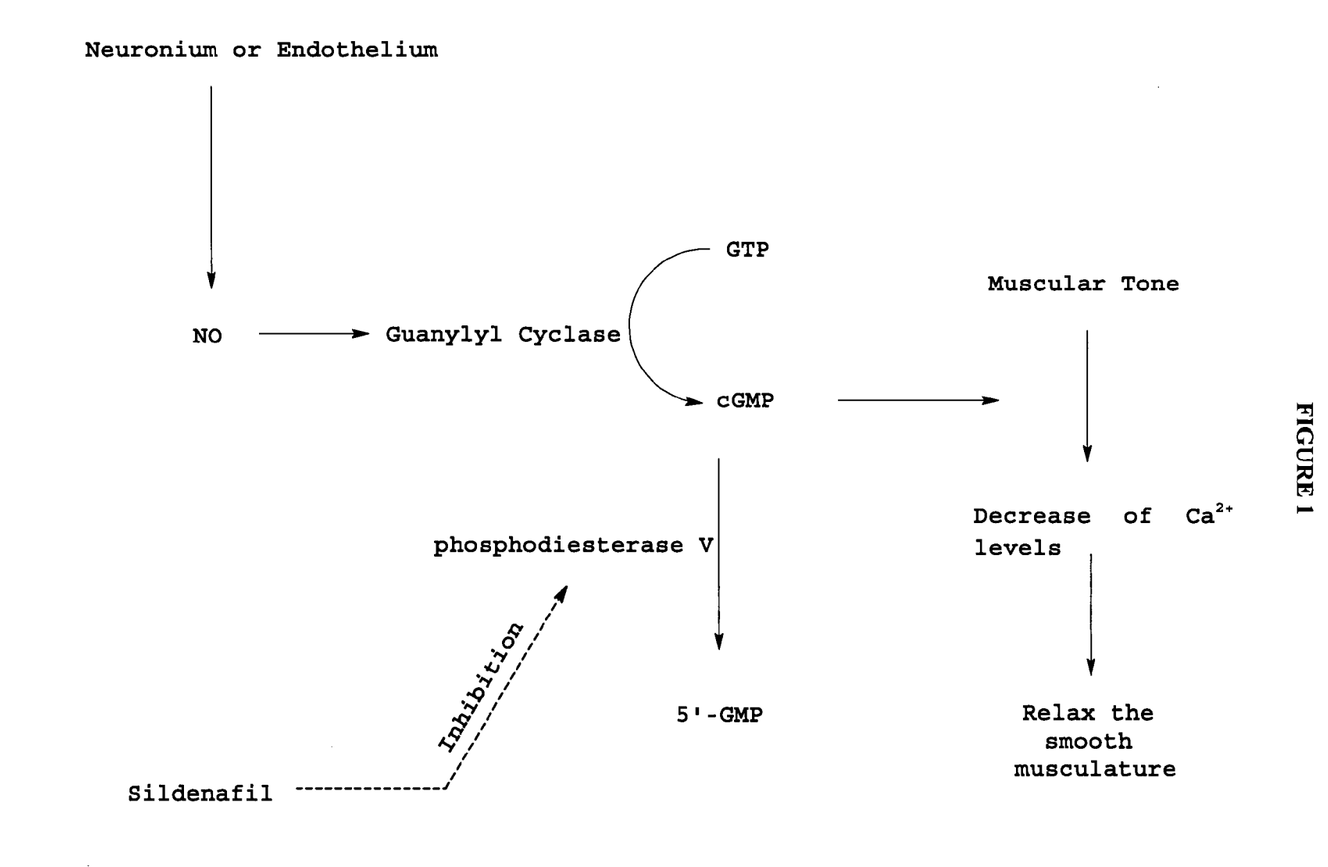
FIG. 1 illustrates the biochemical mechanism of erection.

In accordance with the scheme represented in FIG. 1, the sexual stimulus will normally induce the increase of the nitric oxide levels, which will activate the enzyme guanylate cyclase, which will convert GRP into cGMP. The cGMP, in its turn, is converted in GMP by means of the action of type V enzyme phosphodiesterase. However, the inhibition of the type V phosphodiesterase, shall decrease the conversion of cGMP into GMP, causing an increase of its concentration. This increment in the concentration of cGMP will interfere in order to decrease the concentration of intracellular calcium ions, causing the relaxation of the smooth musculature and of cavernous bodies and arteries, leading to an increase of blood flow into the penis, causing its intumescence.

Another drug recently launched for the treatment of erectile dysfunction is the phentolamine, an adrenergic $\alpha 1$ and $\alpha 2$ blocker, acting directly in the blocking of receptors of existing adrenaline and noradrenaline in the smooth musculature, which are the agents responsible for its contraction. Phentolamine, upon binding to these receptors, prevents the coupling of these hormones, causing the muscular relaxation. This drug was recently launched in an oral formulation. Previously, it was used in injectable formulation together with other drugs for the treatment of erectile dysfunction.

In the contrary of sildenafil, phentolamine is a non-specific drug, exerting its activity within the whole organism and it can interfere in other natural mechanisms, leading to the manifestation of several side effects.

We can find in the literature references describing the administration of real drug cocktails to the patients with erectile dysfunction. Many of them refer to the administration of these cocktails via intracavernous or intraurethral, invasive and not well tolerated by patients.

Among the available treatment in which oral path is the preferential one, the phosphodiestherasis inhibitors, specially the specific type V phosphodiestherasis inhibitors, have a better activity when compared with the other existing therapies. The fact that these medications present a better activity is related to the specificity of their performance when compared to other oral medications. Penis tissues have a high concentration of this enzyme, which activity blocking or its inhibition lead to the increase of the local cGMP levels, triggering the relaxation process of smooth musculature located on these tissues, and this relaxation make possible the penis erection.

Sildenafil is an inhibitor of the type V phosphodiesterase, thus acting as a specific medication in the treatment of erectile dysfunction, as it acts on the inhibition of this enzyme, abundant in penis tissues.

Studies related to the absorption and bioavailability of sildenafil showed that after its administration, this compound is quickly absorbed by the organism, presenting absolute bioavailability of only 40%, due to an extensive degradation promoted by the pre-systemic metabolism. This means that out 100% of the drug administered and absorbed, 60% is turned into metabolites, and only 40% of the original active drug reach systemic stream, being this parcel effectively responsible by the real effect of the drug.

These results give to sildenafil the classification of a drug which pre-systemic metabolizing ranges from intermediate to high, thus presenting intermediate to low oral bioavailability. As a consequence of these factors, more elevated doses of these drugs are necessary for the achievement of the desired effect, what can trigger more severe side effects.

Bioavailability is a parameter having an essential importance when a drug activity is being evaluated. This parameter is related with the drug absorption in the organism and with the type of chemical and enzymatic processes to which this drug will be submitted in the biologic environment, which will act on the original drug, degrading it or turning it in less actives derivatives, toxic derivatives or even completely inactive to the organism.

With the purpose of developing more efficient, more specific drugs presenting a higher activity due to the smaller interference of pre-systemic metabolism, many studies are being performed in several areas, which are generating very promising results concerning to the development of special drugs.

More recently, a new class of drugs is in full development, which involves the obtainment of dimeric or multimeric pro-drugs, which show advantages relating to the original drugs, mainly when the latter present disadvantages relating to the low absorption and/or to the high activity of pre-systemic metabolism in its inactivation, therefore leading to a low bioavailability.

The use of dimeric pro-drugs in the administration of identical, equivalent or complementary drugs is still an emerging practice in the pharmaceutical field.

Invariably, these dimeric pro-drugs present their monomeric units united one to another by means of easily cleaved bonds in biologic environment, being these bonds called labile bonds or bridges. Once introduced in biological environments the labile bonds of these pro-drugs are broken, releasing the active monomeric units, the drugs themselves.

An example of use for different compounds bonded to each other by means of a labile bond is the case of the Scriptene (Clinical Pharmacology and Therapeutics, 59, 184, 1996; Antimicrobial Agents and Chemotherapy, 34, 1061–1067, 1990; J. Clin. Pharmacol., 37(3), 201–213, 1997; Antimicrobial Agents and Chemotherapy, 41(11), 2502–2510, 1997). In this compound, zidovudine (AZT) and didanosine (DDI) were bonded via their 5 bonds with a phosphate bridge, generating the heterodimer AZT-P-DDI. This heterodimer showed to be more powerful and less toxic than AZT. Trials showed that after intravenous administration of AZT-p-DDI (50 or 100 mg), its plasmatic concentration decreased dramatically, no longer being detected after 30 minutes. After oral administration, the dimer was not detected, suggesting an intense gastrointestinal and/or pre-systemic metabolism Specifically in this case, AZT-P-P presents 10 times less toxicity for granulocyte progenitor cells and macrophages, and also more active, $EC_{50}$ of 0.14 nmol/L, when compared with the isolated monomers (3.9 e 460 nmol/L respectively). Thus, a marked improvement related both to toxicity and the increase of the dimer activity in relation to the drugs separately administered was observed. However, oral bioavailability of AZT (64.7–67.3%) and DDI (33.6–42.9%) and other pharmacokinetic parameters were consistent with other studies reported to the drugs separately administered or combined.

These data showed the benefit that can be reached by the use of this medication planning strategy, aiming at the obtainment of more efficient compounds and presenting less side effects than original compounds, due to the lower toxicity of these new chemicals.

We can found in the literature a great variety of patents, which describe the treatment of erectile dysfunction by means of the use of type V phosphodiestherasis inhibitors, wherever jointly or not with other compounds.

Aiming at the increase of the sildenafil bioavailability, there are the patents WO 99/66933 and WO 00/00199, which propose its administration in nasal path compounds. On patent WO 99/66933 the release of sildenafil, its salts or derivatives, alone or in combination with other compounds is proposed, for system circulation by means of a composition to be administered by the intranasal path. In patent WO 00/00199 the use of cGMP phosphodiesterase inhibitors, preferably sildenafil, its salts or derivatives, also by means of compositions for intranasal path. Authors of both patents stated that this route is the most advantageous one, as it avoids the actuation of pre-systemic metabolism action, making possible the setting of desired effect in a time period shorter than the one seen in oral compositions. Authors mention that these compositions present effect within around 15 minutes, against a range from 30 minutes and 2 hours seen in the oral compositions. Authors also state that, due to the avoidance of pre-systemic metabolism, doses lower than the ones used for oral sildenafil can be administered in order to achieve the desired effect. In accordance with these authors, doses ranging from 30 mg and 400 mg of sildenafil can be administered for the obtainment of ideal effect. Considering the fact that the recommended doses for sildenafil orally administered range from 40 mg and 100 mg, one can see that doses recommended in the above mentioned patents in an intranasal administration are much higher than the ones presently employed in oral path treatment, presenting a higher risk of side effects. Another point of extreme relevance refers to the advantage emphasized by authors that the patient would be able to "titer" the effect he wishes to achieve, repeating the doses as required. A possible distraction of the patient concerning the number of times he has self-administered the formulation could lead to a medication overdose, if the drug did not present immediately the expected effect. This possibility would be less likely with the use of oral medication, as there is a more efficient control on the amount of consumed pills.

Patent WO 99/66924 presents the proposal of keeping control of the amount of nitric oxide within the organism by means of donors and sequesters of this substance. The planning strategy described in this patent follows the reasoning of intervention in the erection mechanism, in the sense of making available a higher amount of nitric oxide for activation of the guanylate cylclase, however with no directly acting on enzyme action, thus not acting as specific medications. This patent proposes the maintenance of nitric oxide balance within the whole organism, searching for other activity types by means of actuation in specific organs in order to obtain a pharmacological answer of interest, in no moment presenting a proposal for the treatment of erectile dysfunction.

Patent WO 99/60985 describes compounds in the form of ionic salts formed by a cation, preferably the alprostadile, and an anion, preferably phentolamine and papaverine, among several others possible anions, including sildenafil. Preferred formed salts are the phentolamine alprostadilate and the papaverine alprostadilate. The method for obtainment of the respective salts is described, as well as the pharmaceutical compositions in intraurethral administration carriers. Moreover, the pharmaceutical composition can be added of an anesthetic agent, for instance, lidocaine, employed with the purpose of decreasing sensitiveness in the contact area or the organ with the application instrument. Although authors highlight the possibility of "self-titration" for the medication administration, searching for the ideal effect desired, repeating the administration of the medication as required, one can see the inconvenient of the intraurethral path has small acceptance by patients in the treatment of erectile dysfunction, as patients submitted to this kind of therapy complain about discomfort and pain with this kind of administration. The use of local anesthetic in combination with the composition will not avoid the starting medication administration discomfort, and, during possible subsequent doses, in search of the "self-titration of the desired effect, will represent a higher risk of injury for the anesthetized tissues, with the possibility of starting undesirable inflammatory and infectious pictures.

Patent U.S. Pat. No. 6,037,346 describes methods and formulations for treatment of erectile dysfunction, where active agent, specially the type V phosphodiesterase inhibitors, is formulated with the purpose of avoiding side effects observed in systemic administration. Active agents, among them sildenafil, can be formulated in the form of compositions of intraurethral application, topical application, intracavernous application and transdermal application, being intraurethral application the procedure of choice. In accordance with the authors, the medication can be available in the form of a kit containing the composition and a device for intraurethral administration. As discussed in the previous patent, the intraurethral path has low acceptance by patients in the treatment of erectile dysfunction, due to discomfort and pain associated to this type of administration.

In patent U.S. Pat. No. 4,863,911 a method for erectile dysfunction treatment in males is described, comprising the administration of a really efficient amount of a compound with formula [E-DHC] or a pharmaceutically accepted salt of this compound, where [E] is an estrogen and [DHC] is a reducing salt carrying, in the lipoid form, dihydropyridine⇔pyridinium. U.S. Pat. No. 4,801,587 claims a method to treat impotence that comprehends the application of an ointment to the skin around penis, comprehending a vasodilative agent selected from the group of papaverine, hydralazine, sodium nitroprusiate, phenoxibenzamine or phentolamine, associated to dimethylsulfoxide and a base. The patent U.S. Pat. No. 5,059,603 describes a composition for the treatment of impotence comprehending essentially an effective amount of nitroglycerin, as vasodilator, caffeine, as a vasoconstrictor, an absorption auxiliary agent and a pharmaceutically acceptable carrier. These references show the topic use of several substances described together with other adjuvants for treatment of erectile dysfunction. In these patents, the medication is applied directly on the penis skin and the active agents, upon absorption, present their pharmacological action. However, this way of application has some risks as a function of the variability from an individual to another. The skin permeability varies largely, what makes difficult the correct and assured dose prescription by the physician. In addition, the skin permeability can vary also as a function of time for the same patient. So, changes related to stress, relative air humidity, the use of cosmetics for skin, as well as sweating characteristic for each individual, can change the medication permeability, what makes difficult a sure prescription. The application mode presented in above mentioned patents can also increase markedly the risk of the presence of substances in non-controlled way, in the organism of the sexual partner, so presenting a risk of his/her health. Among these compounds, nitroglycerine, for instance is promptly absorbed by the vaginal mucosa, and it is not possible to control or measure the effects that can arise from a contamination via sexual intercourse.

U.S. Pat. No. 4,127,118 describes a treatment for the masculine impotence by administration by injectable path of administration of vasodilative drugs directly in the cavernous bodies and porous body of the penis, using a syringe and one or more hypodermal needles. This patent suggests, particularly, the application of sympathomimetic agents such as nilidrine, adrenergic blocking agents, such as tolazoline hydrocloride, and vasodilators such as the isoxsuprine hydrocloride and nicotinile alcohol. Even if the injection of vasoactive agents directly in the penis can produce a quick response in patients with erectile dysfunction, we can find numberless reports of psychological disturbances, acute pain, traumatism or inconvenience during sexual intercourse. Other side effects including priapism, nodules in cavernous tissues, fibrosis, tolerance to drugs used, hematomas, ulcerations in skin near to injection application place, among others, are extensively reported in medical literature, being frequent causes for the abandon of injectable therapies.

Patent WO 99/59584 presents compositions and methods for the treatment of erectile dysfunction in humans. The treatment of erectile dysfunction is performed by simultaneous or sequential administration of two active substances, one of them being a vasodilator, phentolamine, and the other a V-type cGMP phosphodiesterase inhibitor, sildenafil. These active substances can be used in their basic forms or in the form of their respective salts, such as citrate, mesylate, hydrochloride, etc. . . . The medication is presented in a kit form, having two different compartments or containers, one of them having the vasodilator, phentolamine, or one of its salts, or an ester derived from it, and another compartment having the V-type cGMP phosphodiesterase inhibitor, sildenafil or an acceptable pharmaceutical salt from it. The different drugs of this kit can be administered simultaneously or sequentially, so that to reach a possible synergistic effect between them. This patent is restrict only to the combination of these to active principles in a kit composed by both medications separated, and it does not present any evolution, as both medications are available in the market. Problems related to the non-specificity of phentolamine and the low bioavailability of sildenafil are not solved and, at the contrary of what is idealized, this type of combination can cause a higher manifestation of side effects than those seen in the use of both drugs separately, as different drugs have different pharmacokinetic and pharmacodynamic profiles, leading to different speeds of manifestation of their effects.

U.S. Pat. No. 5,981,563 present compositions having vasodilator substances, preferably phentolamine, and its respective salts, for oral administration. These are formulated in the form of quick dissolution pills, so that to present improvements in their bioavailability. Agents employed in this patent are non-specific substances in the treatment of erectile dysfunction, exerting its effect in a generalized way within the organism, leading to a low performance of these drugs and to several side effects.

Patent WO 99/64033 describes multiligand compounds that bond to a V-type phosphodiesterase enzyme so that to modulate its activity; The compounds described in this patent are useful for the treatment of diseases and conditions in mammals that are V-type phosphodiesterase-mediated. These compounds are obtained by means of combinatorial chemistry and methods to generate the compound library are also described. The multiligands are obtained in the form of dimers or multimers, however united by means of rigid bonds and not biocleaved. Authors describe that, being the phosphodiesterase an enzyme containing two active sites (on dimer), these compounds, when bind to V-type phosphodiesterase and occupy both active sites of a same enzyme molecule, could cause a deformation in its structure, that could lead to a complementary allosteric inhibition. This patent, spite of presenting dimeric and multimeric compounds for the treatment of the erectile dysfunction, search for another kind of activity to be reached with their use. These compounds are synthesized and employed in the dimeric and multimeric forms, but they do not act as pro-drugs that can be regenerated in active units by means of natural biochemical processes. The effect and activity searched by authors, will certainly face problems associated with absorption and bioavailability of these compounds, as they are molecules with high molecular weight, and so shall continue, without being changed by the organism, so that they can exert this activity. Macromolecules of this kind invariably do not diffuse by tissues in large amounts and, therefore, the doses of this kind of compounds must be extremely high so that they can exert a therapeutic activity, what could cause severe side effects.

Relating to the search of an improvement in the delivery mechanism and medication action, there are in literature several patents that refer specifically to pro-drugs development.

U.S. Pat. No. 5,306,809 presents a set of molecules hydrolitically labile that allow the controlled delivery of biologically active substance into neutral means and or slightly acid in cancerous tissues. These pro-drugs allow the delivery of cytotoxic substances, avoiding numberless problems associated to them. The union bridges between homodimers and heterodimers presented in this patent derive from the anydride of maleic acid. Authors mention that by means of the presence of certain substitutes, electron donors or receptors, one can get higher or lower liability of the bond, which will reflect on higher or lower delivery time of the drug into the organism and therefore change the pharmacodynamics and the pharmacokinetics of the medication. In this specific case, it is desirable that the bond bridge is labile in a slightly acid environment, as cancerous tissues present this property, so the present replacing can be changed so that the proper liability is attained as a function of the desired answer, i.e., as a function of desired delivery time and as a function of place, i.e., into which organ, tissue, or cell the medication must be released. The subject patent does not focus the use of medications for treatment of erectile dysfunction, being specifically related to the use of drugs in cancer treatment.

U.S. Pat. Nos. 4,631,190, 4,997,913, 5,140,013 and 6,030,997 suggest substances sensitive to acid environment conjugated to active molecules, so that the active agent can be selectively delivered to the organs and tissues presenting slightly acid pH, of high effectiveness in chemotherapeutic treatments. Authors suggest the chemical bond of the drug to a biopolymer or to an antibody. This bond must be sensitive to the pH of the environment where the drug is to be released. Antibody segments, immunospecific to the organic system, enable the specific interaction of the macromolecule containing the medication with target tissue cells. Once in the specific region, due to the high specificity of the antibody, the bond sensitive to pH is broken and the pharmacologically active agent is release to act, so obtaining the desired action with side effects markedly decreased, as the chemotherapic agents generally present high cytotoxicity also to the healthy cells. In these patents, we can see that authors are restricted to employ these pro-drugs in the treatment of cancer, and there is no mention to the possible use of the same kind of approach in the development of pro-drugs involving phosphodiesterase inhibitors.

U.S. Pat. No. 6,040,297 presents compounds orally administered, particularly useful as pro-drugs. One of the authors' propositions is to obtain homodimers and heterodimers presenting the monomeric units through phosphate bridges, in order to explore the liability presented by this kind of bond, i.e., the ability of its cleavage in specific regions of the organism. These dimeric substances would act with the purpose of minimizing the effect of pre-systemic metabolism on the monomeric units, which, when used as such, are turned into less active metabolites and sometimes toxic even before they can reach the organ, or the tissue, in the required concentration to obtain the desired pharmacological answer. This patent describes the preparation of pyrophosphates of nucleosides, a method to encapsulate them in biological carriers (particularly erythrocytes), so that to reach specific targets or cell populations involved or responsible for the development of pathological disorders such as tumors or viral infections. In this patent there is no reference to the use of this kind or theory for the use in medications for erectile dysfunction, neither the use of this type of kind of technology for preparation of dimeric substance composed by the phosphodiesterase inhibitors.

U.S. Pat. No. 6,031,096 describes a series of pro-drugs derived from acyclovir, for topical application as antiviral agents in the treatment of infections caused by herpes simplex virus. One of the main barriers for topical application of active medication against infections caused by virus is its small permeability to dermis and epidermis. Some phosphoesters derived from the active agent present better results than the respective compound, as they have higher permeability to skin, reaching in a more efficient way the affected region of the organism. Since the affected region is reached, phosphoesters derivatives from the compound, the pro-drugs proper, suffer conversion into the respective derivative hydroxy or amino of the substance, which are the effectively active agents. This way, the permeability barrier can be overcome by pro-drug that converts into the active agent in the interest region, where then acts. This patent is only about preparation and use of acyclovir pro-drugs, and do not state any kind of approach relating to the use of this kind of technology for preparation of phosphodiesterase inhibiting drugs.

U.S. Pat. No. 6,051,576 describes a series of homo or heterodimers or multimers compounds which present its active units connected via labile bonds. Among the active units that compose these substances, there are several drugs which present the most different properties, as, for instance, anesthetic, analgesic, anti-inflammatory, anti-viral, anti-fungal and modulators of immunologic answer, among others. These compounds can be synthesized in order to present identical active monomeric units, or with similar activities, synergistic or even different. The bond can be established via simple bond between active units or even those can be bonded by means of a polymeric matrix. However, among all the compounds and activities claimed in the mentioned patent, there is no mention to the use of the referred technology for the treatment of erectile dysfunction, or even for the use of compound with activity in the phosphodiesterase inhibition.

There are also some references that approach the possibility of using mechanisms able to increase the bioavailability of sildenafil via inhibition of the enzyme responsible for its extensive degradation, the cytochrome P450. This strategy of pharmacos planning is described in German patents DE 19834505, DE 19834506 and DE 19834507, in which is used the sildenafil together with substances able to inhibit this class of enzymes such as erythromycin, cimetidine, cetoconazole, itraconazole or mibefradil.

Cytochrome P450 corresponds to a family of enzymes that are responsible for bio-oxidative transformations of xenobiotics and endogenous biochemicals. The isoenzyme of cytochrome P450, CYP3A4 is one of the most important human enzymes due to the fact that about 60% of the drugs used are biotransformed, at least partially, by it. In the case of sildenafil, this isoenzyme is the main responsible for its pre-systemic metabolism, and also for the systemic metabolism. In addition to its importance in the sildenafil deactivation, this isoenzyme of cytochrome P450 is responsible for countless other metabolic processes, including the metabolism of a large range of medications, in addition to a series of other endogenous metabolic processes in the human organism. A strategy of inhibition of this enzyme family could change metabolic processes required by other drugs, in addition to interfere directly in natural biochemical processes of our organism.

We shall consider that the target population for treatment of erectile dysfunction corresponds to a special population, most of them being elderly. This population presents a higher statistical incidence of several other kind of troubles, which, many times, are being controlled my means of other drugs. Due to this fact, certainly a strategy leading to the inhibition of an enzyme such as CYP3A4, could not be considered as a safe strategy. This population needs, for maintenance of its life quality, special medications, which can be metabolized by this subject enzyme. Its inhibition could lead to an interference in the sense of increasing the plasmatic concentration of certain medicines, and could cause an increase of its activities in a non-controlled way, leading to the failure of essential organic functions.

Patents listed above show the great variety of research work that are being conducted with the purpose of obtaining more efficient medications, but they do not approach of suggest the ways followed by the present invention aiming at solving the existing problems in the state of the art.

As previously mentioned, one of the main medications developed for the treatment of erectile dysfunction is sildenafil, a specific inhibitor of the V-type phosphodiesterase. This kind of compound exerts its advantage due to the fact of being a specific drug, presenting small activity outside its activity site. However, we mentioned also that its use is very impaired by the extensive action of pre-systemic metabolism on this molecule, what leads to a low bioavailability of the drug.

This actuation of pre-systemic metabolism is responsible for the degradation of about 60% of the effectively active drug, which is turned into several metabolites, between which the main one is called UK 103,320, which structure corresponds to the form N-demethilated of sildenafil, being this one originating from the action of the isoform CYP3A4 of cytochrome enzyme P450.

The possibility of inactivation or inhibition of this enzyme in order to increase the bioavailability of this drug is a remote possibility, due to the endogenous or xenobiotical biochemical process in which it takes part.

On the other hand, the alternatives for resolve the low bioavailability of drugs such sildenafil, up to now, did no present really promising results, regarding to the effective increase of its activity and decrease of side effects.

We can see also that these alternatives has searched only the change of administration route, or changes in the formulations used in the administration of this molecule, or even the search for a possible allosteric modulation of V-type phosphodiesterase.

Up to the moment, there is no reference handling the use of pro-drugs, more specifically dimeric pro-drugs for the treatment of erectile dysfunction using specific phosphodiesterase inhibitors.

As previously mentioned, a new class of substances is in full development, which corresponds to the synthesis of homo or heterodimeric compounds, which present improved properties acting so that to minimize the effect of inactivation from the pre-systemic metabolism of drugs widely degraded by it, influencing positively in the bioavailability of these compounds, in addition to an effective decrease of their toxic profiles, leading to an increased activity together with a decreased manifestation of side effects.

One of the objectives of the present invention is the obtainment of homodimeric or heterodimeric pro-drugs and the pharmaceutically acceptable salts of these pro-drugs, which are rapidly metabolized "in vivo", releasing its active monomeric units.

Particularly, these pro-drugs are synthesized using monomeric units presenting activity in the phosphodiesterase inhibition, specially the V-type phosphodiasterase, being this one another objective of the present invention, the use of these special types of substances in the treatment of diseases or dysfunction that can be mediated by this class of enzymes, or that can be indirectly treated by means of its inhibition.

In particular, these compounds present activity in treatment of erectile dysfunction.

These dimers present the monomeric units bonded by means of a labile bond or bridge, which, through natural organic processes is easily cleaved, regenerating the active monomeric units. Due to the fact that the active drug, or the active drugs are made available by means of natural organic processes, factor such as absorption and bioavailability are positively influenced. As these dimers present the particularity that, upon their regeneration into their active drugs by means of natural processes, on the one hand, they reduce the activity of pre-systemic metabolism relating to drugs inactivation, making possible an effective increment in their bioavailability and, on the other hand, considering the use of drugs with different absorption and bioavailability profiles, that they are naturally released into the organism, by means of breaking these labile bonds, eliminating these inherent differences of absorption or bioavailability among the different substances.

Another factor having important relevance relating to these dimeric substances is related to the gastrointestinal discomfort seen with the use of V-type phosphodiesterases specific inhibitors. I and V-type phosphodiaterases enzymes are expressed also in this organism region and, as the phosphodiesterases inhibit them, this can be the main cause responsible for this gastrointestinal discomfort. The use of these dimeric substances containing phosphodiesterase inhibitors is presented as a form of avoiding this side effect, as no local active drug concentration on the concerned organs will occur.

These dimeric pro-drugs, as previously explained, can be formulated so that the monomeric units present molecules with the same activity profile, and in this case monomers present activity related to phosphodiesterase inhibition.

In these cases, monomers that compose dimers can be chosen among the V-type phosphodiesterase inhibitors, among them the several 1,6-dihydro-7H-pyrazole[4,3-d]pyrimidin-7-one derivatives, among other compounds presenting selective activity for modulation of this phosphodiesterase.

Preferably among the V-type phosphodiesterase inhibitors, are the 1,6-dihydro-7H-pyrazole[4,3-d]pyrimidin-7-one derivatives of formula:

where $R_1$ and $R_2$ are each independently —H, —$C_1$–$C_6$ alkyl, —$C_1$–$C_6$OH, or —$C_1$–$C_6$NHR', wherein R' is —H, or $C_1$–$C_6$ alkyl; $R_3$ is:

wherein $R_4$ is —H, —$C_1$ to $C_6$ alkyl, —$C_1$–$C_6$OH, or —$C_1$–$C_6$NHR'; $R_5$ is —H, —OH, —NHR', $C_1$ to $C_6$ alkyl, —$C_1$–$C_6$OH, or —$C_1$–$C_6$NHR'; or $R_5$ is:

wherein $R_6$ is —H, morpholine, piperidine, hydroxyalkyl piperazine, or aminoalkyl piperazine, wherein alkyl is of $C_1$–$C_6$.

Among the labile bridge or bonds to be established as bonding point among the different monomeric units, we can exemplify the carbamate bridges, carbonate bridges, urea bridges and phosphate bridges, among others presenting the capacity to be naturally biocleaved by the organism via different processes relating to the pre-systemic metabolism, or even other chemical processes in the trajectory of medication within the organism.

The union of these monomeric units by means of these labile bonds can be effectuated via simple bond between two or more monomeric units. However, these monomeric units can present bonded by means of a matrix or natural, polymeric or synthetic reservoir system, biologically compatible with the environment. Such polymeric matrices include, for instance, acetate polyvinyl, polyvinylic alcohol, polyvinylic butyrate, with crossed bonds, ethylene ethyl acrylate copolymer, polyethyl hexyl acrylate, polyvinyl chloride, polyvinyl acetals, ethylene vinyl acetate copolymer, ethylene vinyl chloride copolymer, polyvinylic esters, polyvinyl butyrate, polyvinyl pyrrolidone, polyamides, polyakyl methacrylate, pharmaceutical grade polydimethyl siloxanes, copolymers silicone-carbonate, among many others.

Figure 2:
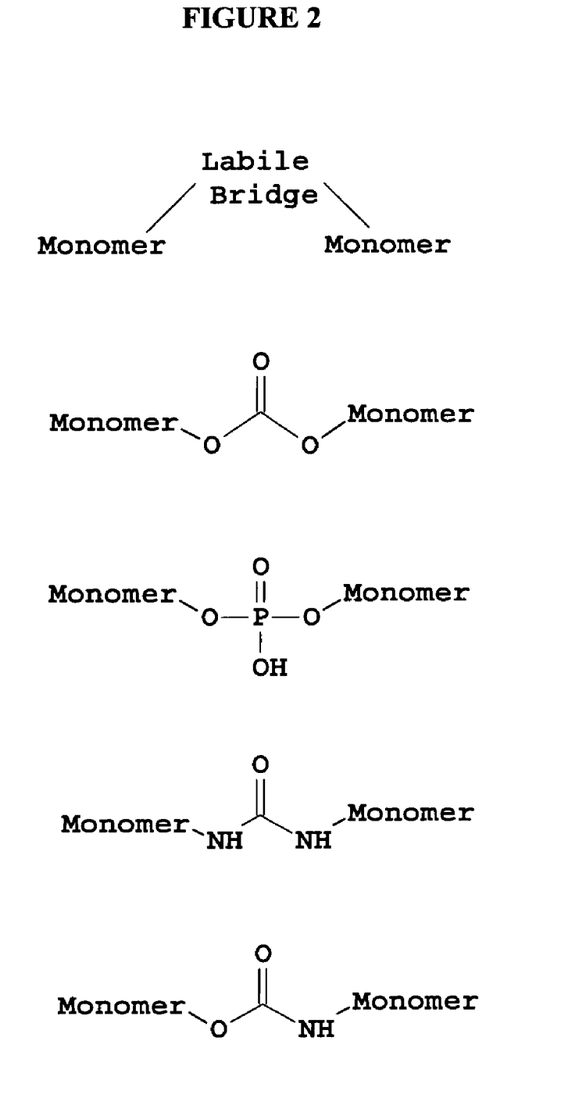
FIG. 2 provides schematic examples of some dimer compounds of the present invention.

Preferably, the monomeric units present bonded to each other via simple chemical bond (labile bridge), forming the dimers The FIG. 2 presents some examples illustrating these compounds.

Another objective of the present invention is the use of these new substances in their forms of acid or basic characters and their pharmaceutically acceptable salts for Medicine and Veterinary.

With this purpose, these compounds can be used in their forms of basic or acid characters, as well as in the forms on non-toxic pharmaceutically acceptable salts, such as hydrochloride, sulfate fumarate, maleate, citrate, succinate, tartarate, acetate, phosphate, benzenesulphonate (besilate), methanesulphonate (mesylate), carbonate, bicarbonate, bitartarate, borate, oleate, lactate, hydrochloride, gluconate, palmitate, palmoate, glutamate, salicylate, estereate and nitrate, among others, when compounds present a basic character. When they are in the acid form, pharmaceutically acceptable salts comprehend the salts derived from alkaline metals, such as sodium and potassium, salts derived from earthy alkaline metals, such as calcium and magnesium, and salts formed with suitable organic ligands, such as ammonium quaternary salts.

Formation of these salts can be effected, e.g., by means of the dissolution of dimeric substances in suitable solvents, together with the addition of the respective acid, whether or not in solution, in order to form the acid addition salt with the compounds having basic character. The same type of procedure can be effected with the acid character compounds, in order to obtain the basic addition salt.

It must be understood that some of the crystalline form of these compounds still may exist as polymorphous and as such they are inserted in the scope of the present invention. Additionally, some of these compounds can form solvates in water (for instance, hydrates), or ordinary organic solvents, and such solvates also are inserted in the scope of this invention.

In a similar way, are inserted in the scope of the present invention all the existing tautomeric forms of these compounds.

Dimeric compounds described in the present invention can be administered to individuals with erectile dysfunction, in therapeutically effective amounts to their treatment. The term individuals refers preferably to humans, however it can also refer to animals, preferably mammals, which are treatment subject, observation or trial. The term therapeutically effective amount is used in the present invention to mean the amount of dimeric pro-drug causing the medical or biological response in animal or human tissue systems, being this response searched for by researchers, veterinarians, physicians or other health professionals, that include the relief or avoidance of symptoms for treated diseases or disorders.

These compounds can be administered to individuals by means of any conventional administration route, including, but not limited to oral, intravenous, subcutaneous, intraurethral, intramuscular, nasal, transdermic, topic, among others. Preferably, the administration route is oral, in order to increase the predisposition of individuals to treatment.

These dimeric pro-drugs can be formulated in the form of pharmaceutical compositions suitable to the administration route. So, these compounds can be formulated in the form of pills, capsules, elixirs, suspensions, syrups, solutions, powders, granules, aerosols, etc.

For preparation of solid compositions, such as pills, the dimeric pro-drug is mixed with pharmaceutical excipients such as, for instance, conventional ingredients for preparation of pills, such as amide, lactose, saccharosis, sorbitol, talc, estearic acid, magnesium estearate, dicalcic phosphate or gums, among numberless others, in addition to other pharmaceutical diluents such as water or an organic solvent, in order to form a composition of homogeneous mix between the compounds described in the present invention or its pharmaceutically acceptable salts. These pills or capsules can still present special coatings so that to protect them from early actions in the course of the medication in the digestive tract. Among the coatings, we can mention the enteric coatings, which protect these medications from an early degradation action in the stomach, allowing its release directly into the duodenum. Among these special coatings, we can mention as example several polymeric acids, such as schellac gum, cellulose acetate and cethylic alcohol.

For preparation of the solution into which these new compounds can be incorporated by oral or injectable administration, we can find aqueous solutions, aromatized syrups, aqueous or oily suspension, aromatized emulsions containing cotton, almond, coconut and sesame oils, in addition to elixirs and similar pharmaceutical vehicles. Proper dispersing agents for aqueous suspensions include natural and synthetic gums, such as tragacanth, acacia, alginate, dextrane, carboxymethyl sodium cellulose, methyl cellulose, polyvinylpyrrolidone or gelatin, among others.

Conventionally for the oral route administration, pharmaceutical formulation can be added by proper pharmaceutical non-toxic excipients such as water, ethanol, glycerol, agglutinants, lubricating agents, disintegrating agents and dies. Among agglutinative agents, we can find amide, gelatin, natural sugars such as glucose or beta-lactose, corn sweetening, synthetic and natural gums such acacia, tragacanth, sodium oleate, sodium estearate, magnesium estearate, sodium benzoate, sodium acetate, sodium chloride and related material. Among disintegrating agents, are amide, methyl cellulose, agar, bentonite, xanthane gum among others.

Liquid formulations can include suspensive agents or aromatized dispersing agents, such as natural or synthetic gums, as, for instance, thragacanth, acacia, methyl cellulose, among others.

For injectable administration are employed sterile solutions or suspensive agents. If the administration is intravenous, isotonic solutions are prepared, with or without the addition of preserving agents.

Recommended doses for the administration of these dimeric pro-drugs will vary, depending on the administration route adopted. Health professionals will evaluate case by case the patient needs, as well as the quality of effect reached, establishing proper doses for the administration route chosen.

For the obtainment of the pro-drugs described in the present invention, 1,6-dihydro-7H-pyrazole[4,3-d]pyrimidin-7-one derivatives shall present chemical functions suitable to the coupling via a labile bond bridge. Among the organic functions that are shown to be proper to this type of coupling, preferably there are alcohols and amines, i.e., molecules presenting, among their replacing agents alcohol and amine functions.

Some of these 1,6-dihydro-7H-pyrazole[4,3-d]pyrimidin-7-one derivatives present their synthesis exemplified in the trial part of the present invention, representative, for exemplification, some of the possible derivatives presenting these type of functions, which can be synthesized in the same conditions described in the present invention, originating active compounds that will be dimerized or condensed, forming the dimeric pro-drugs that are the subject of the present invention.

The synthesis of these dimeric pro-drugs can be achieved by means of usual process for forming bonds of phosphate, carbonate, carbamate or urea, described in references or in organic synthesis compendia.

For the synthesis of pro-drugs described on the present invention, are preferably adopted the procedures using reaction with phosphor oxychlorides or alkyl derived from it, several chloroformates, or even phosgene, reagent able to generate new chloroformates, these ones already derived from active intermediates which shall form the dimeric pro-drugs.

This synthetic approach is widely used in the peptide synthesis, offering a reaction medium generally mild for the obtainment of these compounds.

In the specific case of the present invention, sinthesized pro-drugs present the particularity of present very easily cleaved bond bridges between monomeric units. These labile bonds, if submitted to severe reaction condition, can break during the coupling reaction, occurring the reagent consumption, however without forming these pro-drugs.

These dimerization reactions are preferably conduced in temperatures that can range from $-10°$ C. to $100°$ C., being the ideal temperature chosen based on the stability of the labile bond formed in the reaction medium employed, as well as on the relative reaction speed.

Reactions with chloroformates are usually followed by the use of an equivalent for an amine, in order to consume the HCl generated during the reaction. Usually, secondary and tertiary amines are used with this purpose, for instance the triethylamine and the pyridine.

Among chloroformates that can be employed for the synthesis of these compounds, we can mention the 4-nitrophenyl chloroformate, the benzyl chloroformate, 4-nitrobenzyl chloroformate, vinyl chloroformate, 4-fluorophenyl chloroformate, 4-methoxyphenyl chloroformate, allyl chloroformate, 2-trichloroethyl chloroformate, 2-bromoethyl chloroformate, among others. Preferably, the 4-nitrophenyl chloroformate is employed for these reactions.

Formation reactions of pro-drugs conduced in the presence of phosgene normally are executed at a temperature ranging from $-10°$ C. to $+10°$ C., preferably at temperatures ranging from $-50°$ C. to $+5°$ C., in its starting formation phase of chloroformate derivative from the active intermediate of these pro-drugs. For the formation of the pro-drugs by means of the reactions of these chloroformates intermediately formed, temperatures ranging from $-10°$ to $100°$ C. are employed. In these reactions with phosgene also are employed tertiary amines for the capture of HCl formed during the reaction.

Reaction times are defined by means of the analytic monitoring of reaction medium. As they can depend on factors such as concentration, quantities employed of solvent reagents, raw materials and intermediates, types of stirring up system, of cooling and heating systems, reactors, etc., these reactions can take place in a more accelerated or slower way. Usually, in order to define the reaction time, reliable analytical methods are adopted such as chromatographic method, which can indicate with high reliability whether or not the reaction was completed, since the reaction medium samples, submitted to these analytic methods, indicate if the reaction is already completed, as a function of the intermediate consumption, or formation of the desired compounds, or even through appearance of small amounts of by-products.

Generally speaking, parameters of these reactions are set in order to make the reaction time last no more than 48 hours, so that to avoid to delay the productive process.

In the formation of these pro-drugs, active intermediate generally are used in an approximated ratio of one molar equivalent, when one wishes to obtain heterodimeric forms. This ratio can vary, in the case where hetero multimeric compound obtainment is desired, i.e., that they are formed by more than one kind of active compound (monomeric unit), being used more than one labile bridge to bond them. In these cases, molar equivalent ratios can be the most different as possible, as one can use from several labile bonds in several points of each molecule, as well as use a natural or synthetic organic polymeric matrix to support the different active units in the formation of the pro-drug.

In the obtainment of the homodimers, i.e., the pro-drugs composed of two identical monomeric units, the active agents are used in a molar ratio relative to about double of the condensation agent, i.e., the chloroformates of phosgene. In multimers, the active agents will be employed in an approximated rate of one molar equivalent to the bond points with the polymeric matrix.

Among solvent agents used for the synthesis of these pro-drugs, usually inert solvents to the reaction medium are used, with the property of solubilize totally or partially the active intermediate substances. Among solvents that can be employed, we can find the $C_5$–$C_{12}$ hydrocarbons or blends among them aromatic solvents as benzene, toluene, xylene, the ethers such as diethylic ether, methyl terc-butyl ether, methyl isopropyl ether, butylic ether, tetrahydrofurane, among others, the chlorinated solvents such as dichloromethane and chloroform, among others, ketones, such as, for instance, acetone, methyl isobutyl ketones, among others, dimethyl formamide, tertiary amines such as triethylamine and the pyridine, in addition to blends among these solvents.

To the procedures of purification of these pro-drugs generally above mentioned solvents are used, in addition of solvents such as $C_1$–$C_8$ alcohols, dimethyl formamide, dimethyl acetamide, dimethyl sulphoxide, acetonitrile, or even employing aqueous solutions with suitable pH and temperature control to effectuate their precipitations.

For the obtainment of pharmaceutically acceptable salts of these pro-drugs, procedures are employed usually with a temperature control, as, when temperatures are elevated, a cleavage of these substances can occur due to the low presentation of the environment pH. Usually, these reactions are effected at a temperature ranging from −10° C. to 100° C. with the addition of alcohol, whether or not in solution, and with environment pH control. Solvents employed can be the same solvents described previously, i.e., $C_5$–$C_{12}$ hydrocarbons, or their blends, ethers, cetones, alcohols, aromatic solvents, chlorinated solvents, dimethyl formamide, dimethylacetamide, acetonitrile, dimethyl sulfoxide, alcohols of $C_1$–$C_8$ and blends among these solvents.

As previously described, the obtainment process of homodimeric or heterodimeric pro-drugs can be so summarized: to a reactor equipped with stirring, heating and cooling systems, a 1,6-dihydro-7H-pyrazole[4,3-d]pyrimidin-7-one derivative is added, as monomeric unit, a suitable solvent, under stirring and at a temperature ranging from −100° C. to +100° C. After that, we add the labile bond formation agent in its solid, liquid or gaseous state, diluted in solvents or directly driven in its natural state. To the reaction medium is added a HCl capturing agent and the reaction is monitored through chromatographic methods relating to the formation of intermediate compound having the labile bridge. Upon verification of intermediate compound formation, the second monomeric unit is added, which may or may not be identical to the one employed in the beginning of reaction. Reaction conditions are set and the reaction proceeds, being monitored by means of analytic reliable methods, such as, for instance, the chromatographic ones, relating to pro-drug formation. Upon completion of reaction, the reaction medium is treated in order to isolate the formed dimer, which is purified with the use of usual purification methods, such as the re-crystallization in suitable solvents or purification by means of chromatographic procedures.

Solvents preferably employed in the solubilization of monomeric unit are $C_5$–$C_{12}$ hydrocarbons and blend among them, the aromatic solvents such as benzene, toluene, xylene, or ethers such as diethylic ether, methyl terc-butyl ether, methyl isopropyl ether, butylic ether, tetrahydrofurane, among others, the chlorinated solvents, such as dichloromethane and the chloroform, among others, ketones such as, for instance, acetone, methyl isobutyl ketones, among others, dimethyl formamide, tertiary amines such as triethylamine and pyridine, in addition to blends among these solvents.

As labile bridge forming agents, we can preferably use the phosphor oxychlorides and their alkyl derivatives, phosgene and several chloroformates, such as 4-nitrophenyl chloroformate, benzyl chloroformate, 4-nitrobenzyl chloroformate, vinyl chloroformate, 4-fluorophenyl chloroformate, 4-methoxyphenyl chloroformate, allyl chloroformate, 2-trichloroethyl chloroformate, 2-trichloroethyl chloroformate, 2-bromoethyl chloroformate, among others.

HCl capturing agent added to reaction medium preferably is a secondary or tertiary amine. Solvents employed to the purification of pro-drugs can be $C_5$–$C_{12}$ hydrocarbons and blends among them, aromatic solvents such as benzene, toluene, xylenes, ethers such as diethylic ether, methyl terc-butyl ether, methyl isopropyl ether, butylic ether, tetrahydrofurane, among other, chlorine solvents such as dichloromethane and the chloroform, among others, the ketones such as acetone, methyl isobutyl ketone among others, dimethyl formamide, tertiary amines such as triethylamine and pyridine, alcohols of $C_1$–$C_8$, dimethyl formamide, dimethyl acetamide, dimethyl sulfoxide, acetonitrile, or even employing aqueous solutions with proper pH control, in addition to blends among these solvents.

Experimental part presented below show in a very simplified way, the obtainment of these pro-drugs, representing the kind of procedures used for the obtainment of countless compounds comprehended in the present invention.

In the reactions 1 to 9 we show examples of obtainment of some intermediates (identified as such), which correspond to some among the possible monomeric units to be used in the formation of these new substances, sinthesized in the form of dimeric or multimeric pro-drugs or theirs salts, which exemplifying reactions are described in Examples 1 to 7.

These intermediates and pro-drugs described in experimental part are an illustrative example, but not an exhausting one, for the countless possibilities of obtaining of the several dimeric pro-drugs described in the present invention.

Reaction 1: Synthesis of Piperazine Ethyl Acetate

To a reaction blend containing 100 g (3 Eq, 0.515 mol, MW=194) of piperazine, 26.3 mL (1.1 Eq, 0.189 mol, MW=101, d=0.726) of triethylamine in 200 mL of isopropanol, add to a solution previously prepared of 18.4 mL (1 Eq., 0.172 mol, MW=122.55, d=1.15) of chloroacetate of ethyl in 140 mL of isopropanol under stirring, at room temperature. Keep the reaction medium under stirring, monitoring the reaction termination by means of a chromatography of the thin layer (about 2–3 hours). Add a solution of 40.6 g (0.344 mol) of succinic acid in 140 mL of isopropanol. Keep the system under stirring for about 30 minutes to assure total precipitation of the succinate salt of piperazine formed. Filter this salt and concentrate the filtrate containing the mono and dialkyled derivatives. We obtain a slightly yellowish oil, which is used in later phases without purification.

Mass obtained=33 g

GC/MS: Monoalkylated derivative 72%, and dialkylated 22%.

Reaction 2: Synthesis of N-BOC-Piperazine

On a 2-liter reactor, suspend 200 g of hydrated piperazine (1.03 mol, 3 Eq. MW=194) in 400 mL of isopropanol. Keep the system under stirring at room temperature, and slowly add a solution of 74.9 g (0.34 mol 1 Eq. MW=218) of di-terc-butyldicarbonate in 280 mL of isopropanol. Let the system under stirring, monitoring the termination of reaction by TLC. At the end of the reaction, to the homogeneous solution, add a solution of 81.1 g (0.69 mol MW=118) of succinic acid dissolved in 280 mL of isopropanol. Keep the agitation for about 30 minutes for the piperazine succinate precipitation. This salt is filtered ant the liquid is concentrated under vacuum obtaining an oil, which is dissolved in 300 mL of dichloromethane. Wash this solution with 10% carbonate solution (200 mL) and dry the organic phase with anhydrous sodium sulfate. Solvent is concentrated under vacuum, yielding a white pasty solid.

Mass obtained: 62 g (97%).

Reaction 3: Synthesis of the Ethylformation Piperazine

This compound can be sinthesized by means of the procedure described for obtaining of ethyl acetate piperazine (Reaction 1), using, instead of ethyl chloroacetate, the ethyl chloroformate. In the same ratios in mol used in the synthesis of piperazine ethyl acetate, 38 g are obtained of an oil slightly yellowish, which shows, via CG/MS to be a blend among the monoalkylated and dialkylated derivatives (77% and 22% respectively). This compound is used directly in later phases without purification.

Reaction 4: Synthesis of 5-{2-ethoxy-5-[(4-ethyl acetate 1-piperazinyl)sulfonyl]phenyl}-1-methyl-3-n-propyl-1,6-di-hydro-7H-pyrazole[4,3-d]pyrimidin-7-one.

Suspend 24.6 g (60 mmol, MW=410.9) of 5-(5-chlorosulfonyl-2-etoxyphenyl)-1-methyl-3n-propyl-1,6-dihydro-7H-pyrazole[4,3-d]pyrimidin-7-one in 900 mL of ethanol absolute. Under stirring and at room temperature, add at only one time, a solution containing 31.0 g (3 Eq., 180 mmol MW=172) of N-piperazine ethyl acetate (Reaction 1) dissolved in 150 mL of ethanol absolute. In an interval of 2–10 minutes, all solid is consumed, forming a clean and homogeneous solution, and after that starts the precipitation of the expected product. At the end of the reaction, which lasts 2–3 hours (monitored by chromatography of thin layer), the product is vacuum filtered and the solid is washed with two portions of 50 mL of iced absolute ethanol. 29 g are obtained (yielding=89%) from the product as a white solid of MP=165.5–166.5° C.

Reaction 5: Synthesis of 5-{2-Ethoxy-5-[(4-BOC-1-piperazinyl)sulfonyl]phenyl}-1-methyl-3n-propyl-1,6-dihydro-7H-pyrazole[4,3-d]pyrimidin-7-one.

Suspend 9 g (21.9 mmol) of 5-(5-chlorosulfonyl-2-ethoxyphenyl)-1-methyl-3n-propyl-1,6-di-hydro-7H-pyrazole[4,3-d]pyrimidin-7-one in 390 mL of ethanol. Add to this suspension a solution of 5.4 g (29 mmol) of N-BOC-piperazine (Reaction 2) in 45 mL of ethanol and 18 mL of triethylamine under stirring at room temperature. Keep stirring about 8 to 12 hours and after that vacuum filter the reaction medium. The product obtained as a white solid presents MP=207–210° C. Yield m=12.1 g (98.5%)

Reaction 6: Synthesis of 5-{2-ethoxy-5-[(4-ethylformate 1-piperazinyl)sulfonyl]phenyl}-1-methyl-3-n-propyl-1,6-di-hydro-7H-pyrazole[4,3-d]pyrimidin-7-one.

This compound can be prepared by means of the procedure described under reaction 4, replacing the ethyl piperazine chloroacetate with ethyl piperazine formate. So, starting from 24.6 g (60 mmol, MW=410.9) of 5-(5-chlorosulfonyl-2-ethoxyphenyl)-1-methyl-3n-propyl-1,6-dihydro-7H-pyrazole[4,3-d]pyrimidin-7-one and reacting with 28.5 g (180 mmol MW=158.2) of ethyl piperazine formate, 23.9 g (75%) are obtained of titer compound MP=149–152° C.

Reaction 7: Intermediate 1

5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one.

To a suspension of lithium aluminum hydride (0.74 g 2.2 Eq. MW=37.9) in 25 mL of THF, slowly add, under stirring and at room temperature, a suspension of 5.0 g (9.1 mmol, MW=546.6) of 5-{2-ethoxy-5-[(4-ethyl acetate 1-piperazinyl)sulfonyl]phenyl}-1-methyl-3-n-propyl-1,6-di-hydro-7H-pyrazole[4,3-d]pyrimidin-7-one in 50 mL of THF. The system is maintained under stirring, monitoring the consumption of the product by chromatography of thin layer, until the complete consumption of the starting reagent (about 5–6 hours). Slowly add water to the reaction medium and, when there is no longer release of $H_2$, add HCl 1M regulating pH for 7. Extract the product with 3 200 mL-portions of chloroform, dry with anhydrous sodium sulfate and vacuum concentrate the product. It is obtained 3.8 g of the product as a cream solid MP=183–187° C. yielding 83%. The same was crystallized from methanol and DMF yielding a slightly yellowish solid with melting point at 189–192° C.

Reaction 8: Intermediate 2

5-{2-Ethoxy-5-[(1-piperazinyl)sulfonyl]phenyl}-1-methyl-3-n-propyl-1,6-dihydro-7H-pyrazole[4,3-d]pyrimidin-7-one.

Suspend 12 g (21.4 mmol) of 5-{2-ethoxy-5-[(4-BOC-1-piperazinyl)sulfonyl]phenyl}-1-methyl-3-n-propyl-1,6-di-hydro-7H-pyrazole[4,3-d]pyrimidin-7-one in about 100 mL ethylic ether. Saturate the reaction medium with HCl gas keeping the temperature of the reaction medium between 20–25° C. Upon saturation of the medium, add a solution of potassium carbonate 10%, setting pH to 10. A floccous white solid is obtained, which is separated by filtration, and washed in the funnel itself with water portions and taken to the oven to dry. Yielding m=8.6 g (87%), MP=148–154° C. (literature 161–162° C.).

Reaction 9: Intermediate 3

5-{2-ethoxy-5-[(4-hydroximethyl-1-piperazinyl)sulfonyl]phenyl}-1-methyl-3-n-propyl-1,6-di-hydro-7H-pyrazole[4,3-d]pyrimidin-7-one.

This compound can be obtained by means of the procedure described to the obtainment of Intermediate 1. So starting from 5.0 g (9.3 mmol, MW=532.6) of 5-{2-ethoxy- 5-[(4-ethyl 1-piperazinyl formate)sulfonyl]phenyl}-1-methyl-3-n-propyl-1,6-dihydro-7H-pyrazole[4,3-d]pyrimidin-7-one and using 0.78 g (20.5 mmol MW=37.9) of LiAlH$_4$, at the end of the procedure 3.3 g are obtained from the compound of titer with MP=176–178° C. as a slightly yellowish solid.

EXAMPLE 1A

Homodimer Carbonate of Intermediate 1

In a 50 mL flask, dissolve 0.6 g (2.96 mmol, 1 Eq., MW=201.6) of 4-nitrophenylchloroformate in 10 mL of dichloromethane and cool this solution to 0° C. Take a solution of 3.0 g of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one (5.92 mmol, 2 Eq., MW=506.6) in 10 mL of dichloromethane in an addition funnel. Slowly add this solution in the reaction flask with constant stirring, keeping the temperature of reaction medium at 0° C. After having added about 90% of the volume for the solution contained in the addition funnel, add 0.22 g of triethylamine. Follow the reaction by chromatography until it is completed for the formation of chloroformate intermediate. Then add the dimethylaminopyridine (0.029 g) and 0.22 g of triethylamine. Heat the system to the reflux and follow the final of the reaction by means of chromatography of thin layer. The reaction medium is washed with several 10 mL-portions of solution 10% of potassium carbonate, until the aqueous phase no longer presents color. Organic phase is separated and successively washed with water and sodium chloride solution. Organic phase is dried with anhydrous sodium sulfate, this sulfate is filtered and the organic phase is evaporated to a reduced pressure until the obtainment of titer compound in the form of a slightly yellowish solid. The same was re-crystallized in ethanol/DWF, to obtain a pale white solid.

Yielding m=2.6 g (85%).
Microanalysis: Theoretical C, (54.53%); H, (6.04%); N, (16.24%).
Obtained C, (54.39%); H, (6.10%); N, (16.12%).

EXAMPLE 1B

Homodimer Carbonate of Intermediate 1—Alternative Method

A phosgene solution (3.5 g, 35 mmol) dissolved in 20 mL of toluene was added dropwise to a solution of 2.02 g (4 mmol) of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one, suspended in 44 mL of toluene. The reaction mixture resulting is stirred and followed by chromatography analysis of thin layer every hour until the reagent conversion in its chloroformate was completed. When the analysis indicates the complete consumption of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one, the volatile compounds of the reaction are vacuum removed (solvents and phosgene), yielding the esther chloroformate raw derivative of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one.

The raw chloroformate obtained above (4.0 mmol, 2.27 g) is dissolved in about 30 mL of dichloromethane, to which is added 2.07 g (4.1 mmol) of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one, followed by the addition of 4 mL of dichloromethane containing 450 mg of triethylamine. The reaction mixture is maintained under stirring, being followed by chromatography of thin layer every hour until this indicates the end of the reaction (disappearing of chloroformate derivative). The reaction mixture is then diluted with 60 mL of dichloromethane, washed with NaCl saturated solution, after with sodium bicarbonate saturated solution and again with NaCl saturated solution. Organic phase is separated and dry with anhydrous sodium sulfate. The solvent is then evaporated to dry, yielding the dimer carbonate as a slightly yellowish solid.

This compound is re-crystallized from ethanol:DMF, yielding a pale white solid. Yielding m=3.2 g (76%)
Microanalysis: Theoretical C, (54.53%); H, (6.04%); N, (16.24%);
Obtained C, (54.45%); H, (6.02%); N, (16.17%).

EXAMPLE 2

Homodimer Urea Intermediate 2

This compound can be obtaining using the procedures described in Examples 1A and/or 1B, replacing the Intermediate 1 by the Intermediate 2. In the same conditions described for Intermediate 1 in the Example 1A, the Intermediate 2 is used in a molar ratio identical to the one described in the mentioned example, 2.49 g (89%) are obtained from the titer compound as a pale white solid.

Under molar conditions described in Example 1B, 2.66 g (69%) are obtained from the titer compound as a pale white solid.

Microanalysis: Theoretical C, (53.57%); H, (5.75%); N, (17.75%).
Obtained C, (53.50%); H, (5.76%); N, (17.72%).

EXAMPLE 3

Homodimer Carbonate of the Intermediate 3

This compound is obtained by means of the procedure described in examples 1A and 1B, replacing Intermediate 1 with Intermediate 3. In the described molar conditions, the yielding for Example 1 A is 2.5 g (84%) and for Example 1B is 3 g (73%).

Microanalysis: Theoretical: C, (53.66%); H, (5.80%); N, (16.69%).
Obtained C, (53.58%); H, (5.73%); N, (16.64%).

EXAMPLE 4

Heterodimers Carbamate between Intermediates 1 and 2

This compound can be obtained by means of procedures described for examples 1A and 1B, with due changes of reagents so to obtain these heterodimers.

EXAMPLE 4A

In a 50 mL reactor, dissolve 0.6 (2.96 mmol, 1 Eq., PM=201.6) of 4-nitrophenylchloroformate in 10 mL of dichloromethane and cool the reaction medium to 0° C. By means of an addition funnel, slowly add a solution of 1.5 g (2.96 mmol, 1 Eq., PM=504.6) of 5-{2-Ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one (Intermediate 1) in 10 mL of dichloromethane and 3.0 g (3.0 mmol PM=101.19) of triethylamine, maintaining the temperature of reaction medium at 0° C. After addition, the reaction medium was maintained under stirring and the same was monitored via thin layer chromatography until complete consumption of reagents. Then, a solution is added, containing 1.37 g (2.96 mmol, PM=460.6) of 5-{2-Ethoxy-5-[(1-piperazinyl)sulfonyl]phenyl}-1-methyl-3-n-propyl-1,6-dihydro-7H-pyrazole[4,3-d]pyrimidin-7-one (Intermediate 2) in 10 mL of dichloromethane and the reaction medium is maintained under stirring under mild heating (about 35° C.) until completion of the reaction (monitored by thin layer chromatography). Upon completion of the reaction, reaction medium is washed with 4 portions of 10 mL of 10% potassium carbonate and thereafter washed with concentrated solution of sodium chloride and after washed with water. The organic phase is dried with an anhydrous sodium sulfate, and solvent is evaporated at reduced pressure, yielding a yellowish solid, which is recrystallized of ethanol, yielding 2.3 g (η=78%) from titer compound as a white solid.

Microanalysis: Theoretical C, (54.53%); H, (5.90%); N, (16.96%).

Obtained: C, (54.48%); H, (5.88%); N, (16.92%).

EXAMPLE 4B

A phosgene solution (3.5 g, 35 mmol) dissolved in 20 mL of dichloromethane was added, dropwise, to a solution of 2.02 g (4 mmol) of 5-{2-ethoxy-5-[(4-hydroxyethyl-1-1-piperazinyl)sulfonyl]phenyl}-1-methyl-3-n-propyl-1,6-dihydro-7H-pyrazole[4,3-d]pyrimidin-7-one (Intermediate 1), dissolved in 44 mL of dichloromethane. The reaction mixture is stirred and followed by thin layer chromatographic analysis every hour, until reagent conversion completes in its chloroformate. When the result of the analysis indicate the complete consumption of 5-{2-ethoxy-5-[(4-hydroxyethyl-1-piperazinyl)sulfonyl]phenyl}-1-methyl-3-n-propyl-1,6-dihydro-7H-pyrazole[4,3-d]pyrimidin-7-one, volatile compounds of the reaction are vacuum removed (solvents and phosgene) yielding the chloroformate ester raw derivative from 5-{2-ethoxy-5-[(4-hydroxyethyl-1-piperazinyl) sulfonyl]phenyl}-1-methyl-3-n-propyl-1,6-dihydro-7H-pyrazole[4,3-d]pyrimidin-7-one.

Above obtained raw chloroformate (4.0 mmol, 2.27 g) is dissolved in about 30 mL of dichloromethane, to which is added 1.84 g (4.0 mmol) of 5-{2-ethoxy-5-[(1-piperazinyl) sulfonyl]phenyl}-1-methyl-3-n-propyl-1,6-dihydro-7H-pyrazole[4,3-d]pyrimidin-7-one (Intermediate 2), and 450 mg of triethylamine. Reaction mixture is maintained under stirring, being followed by thin layer chromatography every hour until it indicates the end of the reaction (disappearing of chloroformate derivative). Reaction mixture is then diluted with 60 mL of dichloromethane, washed with NaCl saturated solution, after with a sodium bicarbonate saturated solution and again with NaCl saturated solution. The organic phase is separated and dried with anhydrous sodium sulfate. Solvent is then evaporated until dry yielding the heterodimer carbamate as a slightly yellowish solid.

This compound is recrystallized from ethanol, yielding 3.1 g (78%) of titer compound with a white solid.

EXAMPLE 5

Heterodimer Carbamate between Intermediates 3 and 2

This compound can be obtained by means of the procedures described in Examples 4A and 4B, replacing Intermediate 1 with 5-{2-ethoxy-5-[(4-hydroximethyl-1-piperazinyl)sulfonyl]phenyl}-1-methyl-3-n-propyl-1,6-dihydro-7H-pyrazole[4,3-d]pyrimidin-7-one (Intermediate 3). In the same conditions of Reaction 4A, 2.55 g (88%) were obtained as a pale white solid. In 3B reaction conditions, 2.74 g (70%) were obtained as a white solid.

Microanalysis: Theoretical C, (54.08%); H, (5.78%); N, (17.20%).

Obtained C, (54.01%); H, (5.76%); N, (16.15%).

EXAMPLE 6

Heterodimer Carbonate between Intermediate 1 and 3

Thus compound can be obtained by means of the procedure described in reactions 4 A and 4B, using Intermediates 1 and 3, respectively in each procedure. Under conditions described, 2.75 g (91%) are obtained as a white solid, by means of Reaction 4A and 3.39 g (83%) from a white solid by means of reaction 4B.

Microanalysis: Theoretical C, (54.10%); H, (5.92%); N, (16.46%).

Obtained C, (54.08%); H, (5.89%); N, (16.44%).

EXAMPLE 7

Obtainment of Salt Citrate of Homodimer Obtained with Intermediate 1

In a 50 mL reaction, suspend 1.1 g (1.06 mmol) of the dimer obtained in Example 2 in 12 mL of ethanol. Add to this suspension 30 mL of a solution containing 0.422 g (2.2 mmol) of citric acid slowly, under mild heating. Keep reaction medium under stirring during about 10 minutes, or until complete dissolution of the solids and cool in ice and salt bath (about −5° C.). Keep stirring during about half an hour. Vacuum filter the precipitated crystals and wash with 2 10-mL portions of absolute ethanol. Take to an oven to dry. 1.34 g of salt citrate of this dimer is obtained, as a white solid. Yielding η=89%.

The invention claimed is:

1. A homo or heterodimer prodrug wherein both monomeric units are 1,6-dihydro-7H-pyrazolo[4,3-d]pyrimidin-7-one compounds of the formula:

wherein $R_1$ and $R_2$ are each independently —H, —$C_1$–$C_6$ alkyl, —$C_1$–$C_6$OH, or —$C_1$–$C_6$NHR' wherein R' is —H, or —$C_1$–$C_6$ alkyl; $R_3$ is:

wherein $R_4$ is —H, —$C_1$–$C_6$ alkyl, —$C_1$–$C_6$OH, or —$C_1$–$C_6$NHR'; $R_5$ is —H, —OH, —NHR', —$C_1$–$C_6$ alkyl, —$C_1$–$C_6$OH, or —$C_1$–$C_6$NHR', or $R_5$ is:

wherein $R_6$ is morpholine, piperidine, hydroxyalkyl piperazine, or aminoalkyl piperazine, wherein alkyl is of $C_1$–$C_6$; with the proviso that each monomeric unit has only one functional group alcohol, primary amine or secondary amine through which the monomeric units are coupled to each other via a labile carbonate (—O—COO—), carbamate (—O—CO—N—), urea (—N—CO—N—) or phosphate (—O—POO—O—) moiety.

2. The homo or heterodimer prodrug in accordance with claim 1, in the form of its pharmaceutically acceptable salt.

3. The homo or heterodimer prodrug in accordance with claim 2, wherein the pharmaceutically acceptable salt is selected from the group consisting of hydrochloric, sulfate, fumarate, maleate, citrate, succinate, tartrate, acetate, phosphate, benzenesulfonate (besylate), methanesulfonate (mesylate), carbonate, bicarbonate, bitartrate, borate, oleate, lactate, dihydrochloric, gluconate, palmitate, palmoate, glutamate, salicylate, stearate and nitrate salts.

4. The homo or heterodimer prodrug in accordance with claim 2, wherein the pharmaceutically acceptable salt is selected from the group consisting of salts derived from alkaline metals, earthy alkaline metals, and salts formed with suitable organic ligands.

5. The homo or heterodimer in accordance with claim 4, wherein the salt formed with suitable organic ligands is an ammonium quaternary salt.

6. The homo or heterodimer prodrug in accordance with claim 1 wherein the monomeric units are 1,6-dihydro-7H-pyrazolo[4,3-d]pyrimidin-7-one compounds having inhibitory activity to type V phosphodiesterase.

7. A homo or heterodimer prodrug consisting of the formula:

or a pharmaceutically acceptable salt thereof, wherein $R_1$ and $R_3$ are each independently —$C_1$–$C_6$ alkyl;
$R_2$ is —H or —$C_1$–$C_6$ alkyl;
$R_4$ is —$C_1$–$C_6$ alkyl, —S(O)$_2$—, —CO—, or —SO—;
L is —CO—, —(CH$_2$)$_n$—O—CO—O—(CH$_2$)$_m$—, —(CH$_2$)$_n$—NH—CO—NH—(CH$_2$)$_m$—, —(CH$_2$)$_n$—O—CO—NH—(CH$_2$)$_m$—, —(CH$_2$)$_n$—O—CO—, —(CH$_2$)$_n$—NH—CO— or —(CH$_2$)$_n$—O—PO$_2$—O—(CH$_2$)$_m$— wherein n and m are each independently an integer from 1 to 6, and wherein L includes or forms a labile carbonate, carbamate, urea or phosphate moiety.

8. The homodimer prodrug of claim 7 selected from the group consisting of:
bis-(2-{4-[4-ethoxy-3-(1-methyl-7-oxo-3-propyl-6,7-dihydro-1H-pyrazolo[4,3-d]pyrimidin-5-yl)-benzenesulfonyl]piperazin-1-yl}-ethyl) carbonate;
5-{2-ethoxy-5-{4-[4-[3-(6,7-dihydro-1-methyl-7-oxo-3-propyl-1H-pyrazolo[4,3-d])pyrimidin-5-yl-4-ethoxy-benzenesulfonyl]-piperazine-1-carbonyl]-piperazine-1-sulfonyl}-phenyl}-6,7-dihydro-1-methyl-3-propyl-1H-pyrazolo[4,3-d]pyrimidin-7-one,
bis-{4-[4-ethoxy-3-(1-methyl-7-oxo-3-propyl-6,7-dihydro-1H-pyrazolo[4,3-d]pyrimidin-5-yl)-benzenesulfonyl]piperazin-1-yl}-methyl carbonate.

9. The heterodimer prodrug of claim 7 selected from the group consisting of:
4-[4-Ethoxy-3-(1-methyl-7-oxo-3-propyl-6,7-dihydro-1H-pyrazolo[4,3-d]pyrimidin-5-yl)-benzenesulfonyl]-piperazine-1-carboxylic acid 2-{4-[4-ethoxy-3-(1-methyl-7-oxo-3-propyl-6,7-dihydro-1H-pyrazolo[4,3-d]pyrimidin-5-yl)-benzenesulfonyl]-piperazin-1-yl}-ethyl ester;
4-[4-Ethoxy-3-(1-methyl-7-oxo-3-propyl-6,7-dihydro-1H-pyrazolo[4,3-d]pyrimidin-5-yl)-benzenesulfonyl]-piperazine-1-carboxylic acid {4-[4-ethoxy-3-(1-methyl-7-oxo-3-propyl-6,7-dihydro-1H-pyrazolo[4,3-d]pyrimidin-5-yl)-benzenesulfonyl]-piperazin-1-yl}-methyl ester; and
2-{4-[4-ethoxy-3-(1-methyl-7-oxo-3-propyl-6,7-dihydro-1H-pyrazolo[4,3-d]pyrimidin-5-yl)benzenesulfonyl]-piperazin-1-yl}-ethyl 4-[4-ethoxy-3-(1-methyl-7-oxo-3-propyl-6,7-dihydro-1H-pyrazolo[4,3-d]pyrimidin-5-yl)benzenesulfonyl]-piperazin-1-yl methyl carbonate.

10. A homo or heterodimer prodrug consisting of the formula:

or a pharmaceutically acceptable salt thereof, wherein
X is oxygen or carbon;
$R_2$ is —H or alkyl of —$C_1$–$C_6$ ;
$R_3$ is —$C_1$–$C_6$ alkyl;
$R_4$ is —$C_1$–$C_6$ alkyl, —$S(O)_2$—, —CO— or —SO—;
L is —CO—, —$(CH_2)_n$—O—CO—O—$(CH_2)_m$—, —$(CH_2)_n$—NH—CO—NH—$(CH_2)_m$—, —$(CH_2)_n$—O—CO—NH—$(CH_2)_m$—, —$(CH_2)_n$—O—CO—, —$(CH_2)_n$—NH—CO— or —$(CH_2)_n$—O—$PO_2$—O—$(CH_2)_m$— wherein n and m are each independently an integer from 1 to 6, and wherein L includes or forms a labile carbonate, carbamate, urea or phosphate moiety.

11. A homo or heterodimer prodrug consisting of the formula:

or a pharmaceutically acceptable salt thereof, wherein
X is oxygen or carbon;
$R_1$ is —$C_1$–$C_6$ alkyl;
$R_2$ is —H, —$C_1$–$C_6$ alkyl;
$R_4$ is —$C_1$–$C_6$ alkyl, —$S(O)_2$—, —CO— or —SO—;
L is —CO—, —$(CH_2)_n$—O—CO—O—$(CH_2)_m$—, —$(CH_2)_n$—NH—CO—NH—$(CH_2)_m$—, —$(CH_2)_n$—O—CO—NH—$(CH_2)_m$—, —$(CH_2)_n$—O—CO—, —$(CH_2)_n$—NH—CO— or —$(CH_2)_n$—O—$PO_2$—O—$(CH_2)_m$— wherein n and m are each independently an integer from 1 to 6, and wherein L includes or forms a labile carbonate, carbamate, urea or phosphate moiety.

12. A homo or heterodimer prodrug consisting of the formula:

or a pharmaceutically acceptable salt thereof, wherein
X is oxygen or carbon;
$R_1$ is —$C_1$–$C_6$ alkyl;
$R_3$ is —$C_1$–$C_6$ alkyl;
$R_4$ is —$C_1$–$C_6$ alkyl, —$S(O)_2$—, —CO— or —SO—;
L is —CO—, —$(CH_2)_n$—O—CO—O—$(CH_2)_m$—, —$(CH_2)_n$—NH—CO—NH—$(CH_2)_m$—, —$(CH_2)_n$—O—CO—NH—$(CH_2)_m$—, —$(CH_2)_n$—O—CO—, —$(CH_2)_n$—NH—CO— or —$(CH_2)_n$—O—$PO_2$—O—$(CH_2)_m$— wherein n and m are each independently an integer from 1 to 6, and wherein L includes or forms a carbonate, carbamate, urea or phosphate moiety.

13. A pharmaceutical composition comprising an effective amount of the prodrug of claim 1, or a pharmaceutically acceptable salt thereof, in admixture with one or more pharmaceutically acceptable excipients.

14. A method for inhibiting type V phosphodiesterase activity, which comprises administering to a mammal in need thereof an effective amount of the prodrug of claim 1 or a pharmaceutically acceptable salt thereof which releases in vivo a type V phosphodiesterase inhibitor.

15. The method in accordance with claim 14, wherein said mammal is a human.

16. A method for treating erectile dysfunction in a mammal in need thereof, which comprises administering to said mammal the prodrug of claim 1 or a pharmaceutically acceptable salt thereof in an effective amount to release in vivo a type V phosphodiesterase inhibitor.

17. The method in accordance with claim 16, wherein said mammal is a human.

18. A process for obtaining the homo or heterodimer prodrug of claim 1 comprising a first monomeric unit and a second monomeric unit wherein said process comprises the steps of:

(a) Adding to a reactor with stirring, cooling and heating systems, the first monomeric unit and a solvent, under stirring within a temperature range from −10° C. to +100° C.;

(b) Adding a linker-forming agent selected from the group consisting of phosgene, carbonyldiimidazole, 4-nitrophenyl chloroformate, phosphorus oxychloride or an alkyl derivative of phosphorus oxychloride, diluted in a solvent or directly in the natural state to the reaction medium, followed by an acid scavenger if the linker-forming agent generates an acid;

(c) Keeping the system under stirring monitoring the coupling between the first monomer and the linker-forming agent by a chromatographic method;

(d) Adding to the reaction medium a defined amount of the second monomeric unit;

(e) Keeping the reaction medium obtained in (d) under stirring within a temperature range from −10° C. to +100° C., monitoring the formation of the prodrug by a chromatographic method;

(f) Obtaining the prodrug by means of suitable treatment of the reaction medium; and (g) Purifying the prodrug.

19. The process in accordance with claim 18, wherein in steps (a) and (d), the monomeric units are 1,6-dihydro-7H-pyrazolo[4,3-d]pyrimidin-7-one compounds as defined in claim 1.

20. The process in accordance with claim 18, wherein in step (a), the solvent employed is selected from the group consisting of hydrocarbon solvents, aromatic solvents, ethers, chlorinated solvents, ketones, dimethylformamide, tertiary amines, and blends among these solvents.

21. The process in accordance with claim 20 wherein said hydrocarbon solvents are those consisting of $C_5$–$C_{12}$ hydrocarbons.

22. The process in accordance with claim 20 wherein said aromatic solvents are benzene, toluene or xylene.

23. The process in accordance with claim 20 wherein said ether solvents are diethyl ether, methyl tert-butyl ether, methyl isopropyl ether, butyl ether or tetrahydrofuran.

24. The process in accordance with claim 20 wherein said chlorinated solvents are dichloromethane or chloroform.

25. The process in accordance with claim 20 wherein said ketone solvents are acetone or methyl isobutyl ketone.

26. The process in accordance with claim 20 wherein said tertiary amines solvents are triethylamine or pyridine.

27. The process in accordance with claim 18, wherein in step (b) the agent employed to capture HCl is a secondary or tertiary amine.

28. The process in accordance with claim 18, wherein in step (g), the prodrug is purified by recrystallization from a solvent selected from the group consisting of hydrocarbon solvents, aromatic solvents, ethers, chlorinated solvents, ketones, dimethylformamide, tertiary amines, alcohols, dimethylacetamide, dimethyl sulfoxide, acetonitrile, aqueous solutions with suitable pH control, and blends among these solvents.

29. The process in accordance with claim 28 wherein said hydrocarbon solvents are those consisting of $C_5$–$C_{12}$ hydrocarbons.

30. The process in accordance with claim 28 wherein said aromatic solvents are benzene, toluene or xylene.

31. The process in accordance with claim 28 wherein said ether solvents are diethyl ether, methyl tert-butyl ether, methyl isopropyl ether, butyl ether or tetrahydrofuran.

32. The process in accordance with claim 28 wherein said chlorinated solvents are dichloromethane or chloroform.

33. The process in accordance with claim 28 wherein said ketone solvents are acetone or methyl isobutyl ketone.

34. The process in accordance with claim 28 wherein said tertiary amines solvents are triethylamine or pyridine.

35. The process in accordance with claim 28 wherein said alcohols solvents are those consisting of $C_1$–$C_8$ alcohols.

* * * * *